US012693028B2

(12) United States Patent
Tran et al.

(10) Patent No.: US 12,693,028 B2
(45) Date of Patent: Jul. 28, 2026

(54) TOROIDAL VORTICES FOR TEMPERATURE-RELATED AND NON-TEMPERATURE-RELATED FUNCTIONS

(71) Applicant: Samsung Electronics Co., Ltd., Suwon-si (KR)

(72) Inventors: Forrest Tran, Milpitas, CA (US); Ian Parker, Santa Barbara, CA (US); Vishnu Venugopal, Sunnyvale, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 354 days.

(21) Appl. No.: 18/386,757

(22) Filed: Nov. 3, 2023

(65) Prior Publication Data

US 2025/0146677 A1 May 8, 2025

(51) Int. Cl.
| | |
|---|---|
| *F24F 1/0011* | (2019.01) |
| *A61L 9/12* | (2006.01) |
| *B08B 5/00* | (2006.01) |
| *F15D 1/00* | (2006.01) |
| *F24F 1/008* | (2019.01) |
| *F24F 120/12* | (2018.01) |

(52) U.S. Cl.
CPC ............... *F24F 1/0011* (2013.01); *A61L 9/12* (2013.01); *B08B 5/00* (2013.01); *F15D 1/009* (2013.01); *F24F 1/008* (2019.02); *A61L 2209/16* (2013.01); *F24F 2120/12* (2018.01)

(58) Field of Classification Search
CPC ...... F24F 1/0011; F24F 1/008; F24F 2221/46; F24F 2120/12; F15D 1/009; A61L 9/12; A61L 2209/16; B08B 5/00; B05B 1/005
See application file for complete search history.

(56) References Cited

U.S. PATENT DOCUMENTS

| | | | | | |
|---|---|---|---|---|---|
| 5,174,967 | A | * | 12/1992 | Fukuhara | A61L 9/14 261/DIG. 65 |
| 2007/0261438 | A1 | * | 11/2007 | Ezaka | B60H 3/0028 62/643 |

FOREIGN PATENT DOCUMENTS

| | | | | | |
|---|---|---|---|---|---|
| CN | 101571302 | A | * | 11/2009 | F24F 11/79 |
| CN | 111609464 | B | | 4/2022 | |
| CN | 114963450 | A | * | 8/2022 | F24F 11/61 |
| CN | 218093737 | U | | 12/2022 | |
| CN | 114100889 | B | | 3/2023 | |
| CN | 219036826 | U | | 5/2023 | |
| CN | 116202164 | A | | 6/2023 | |
| WO | WO-2010016177 | A1 | * | 2/2010 | F24F 8/00 |

(Continued)

OTHER PUBLICATIONS 333 (Year: 1999).*
222 (Year: 1999).*
444 (Year: 1999).*

*Primary Examiner* — William C Doerrler

(57) ABSTRACT

In one embodiment, a method includes receiving air into a device that includes an actuator for generating one or more toroidal vortices and determining whether to generate a toroidal vortex for conditioning air in an environment of the device or whether to generate a toroidal vortex for a non-temperature-related functionality. The method further includes generating, based on the determination and by the actuator, one or more toroidal vortices and transmitting, by the device, the one or more toroidal vortices into the environment.

19 Claims, 4 Drawing Sheets

(56) References Cited

FOREIGN PATENT DOCUMENTS

| | | | | |
|---|---|---|---|---|
| WO | WO-2020075854 A1 * | 4/2020 | ............ | F24F 11/755 |
| WO | WO-2021050369 A1 * | 3/2021 | ........... | G06V 40/103 |

* cited by examiner

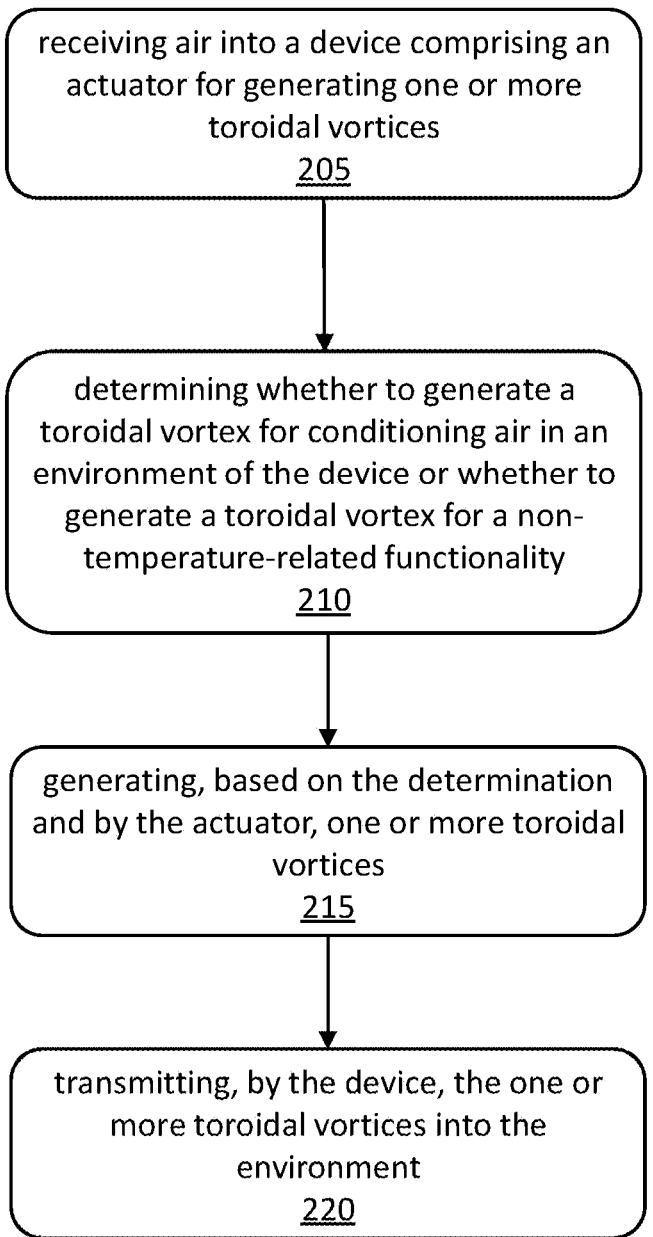

receiving air into a device comprising an actuator for generating one or more toroidal vortices
205 determining whether to generate a toroidal vortex for conditioning air in an environment of the device or whether to generate a toroidal vortex for a non-temperature-related functionality
210 generating, based on the determination and by the actuator, one or more toroidal vortices
215 transmitting, by the device, the one or more toroidal vortices into the environment
220

Fig. 2

TOROIDAL VORTICES FOR TEMPERATURE-RELATED AND NON-TEMPERATURE-RELATED FUNCTIONS

TECHNICAL FIELD

This application generally relates to toroidal vortices for temperature-related and non-temperature-related functions.

BACKGROUND

Toroidal vortices, also known as vortex rings, are moving, stable structures that can form in fluids, such as in ambient air. A toroidal vortex is a torus-shaped vortex in a fluid, and a toroidal vortex is typically defined by a region where the fluid in the vortex mostly spins around an axis line that forms a closed loop. The dominant flow in a vortex ring is typically in the poloidal direction.

A vortex ring typically moves in a direction that is perpendicular to the plane of the ring such that the inner edge of the ring moves forward faster than does the outer edge. Within a stationary body of fluid, a vortex ring can travel for relatively long distance, carrying the spinning fluid with it.

BRIEF DESCRIPTION OF THE DRAWINGS

FIG. 2 illustrates an example method for generating toroidal vortices.

DESCRIPTION OF EXAMPLE EMBODIMENTS

Temperature control (i.e., heating and cooling) of ambient spaces in homes, office buildings, and other structures consumes a great deal of energy. Temperature control can result in significant monetary costs, and the energy consumption required to control ambient temperatures can result in significant emissions, such as $CO_2$ gases. People typically only occupy a small fraction of the volume of a structure at any given time, yet traditional approaches to temperature control attempt to adjust the temperature of the air in the entire volume of the structure or in the entire volume of a room. In addition, traditional approaches to temperature control provide no way for people to personalize the temperature of the particular space they are in. For example, if two people are in the same room, that room's temperature-control systems (e.g., a heating, ventilation, and air conditioning system or "HVAC" system) will tend to heat or cool the entire room to the same temperature, even though the two people may have different temperature preferences.

Systems and methods of this disclosure use toroidal vortices to provide temperature control of a space. As explained below, using toroidal vortices to control temperature provides much more precise heating and cooling of spaces that a particular person is located in. In addition, as explained below, the systems and methods of this disclosure use toroidal vortices to provide non-temperature-related functionality, such as dusting, reminders, aroma control, and other functions.

Figure 1:
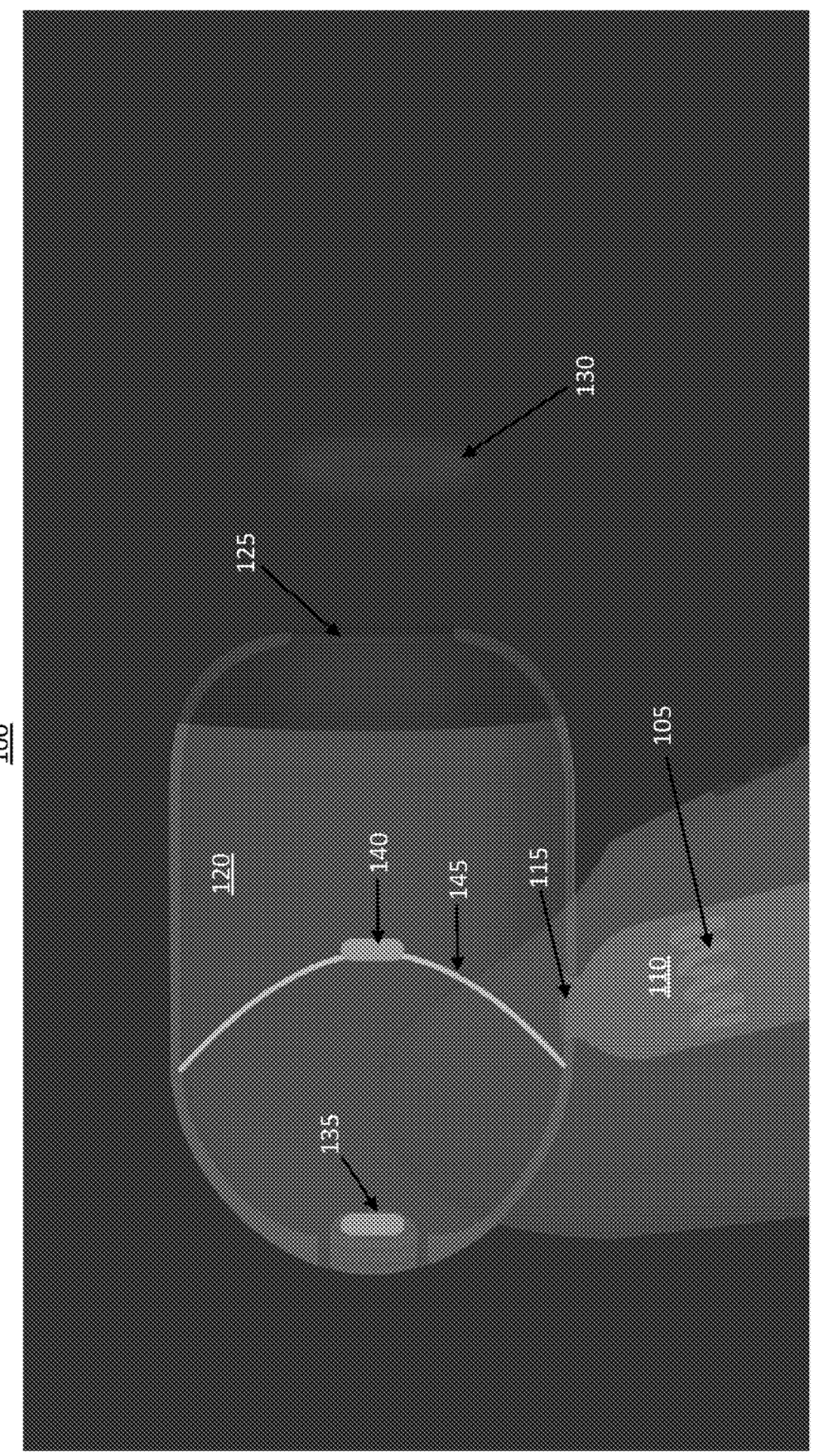
FIG. 1 illustrates an example device for generating toroidal vortices.

FIG. 1 illustrates an example device 100 for generating toroidal vortices. In the example of FIG. 1, device 100 includes a heating element 105 for heating air flowing through passage 110. The heated air flows through inlet 115, which may be a one-way valve or may be an actuated aperture, such as an iris. After flowing through inlet 115, heated air arrives in cavity 120, which has a rounded shape in order to generate vortex rings. Air may be drawn into passage 110 through any suitable mechanism including ducting, fans, pumps, and passive intakes. While the example of FIG. 1 illustrates device 100 as having a heating element, this disclosure contemplates that device 100 may have any suitable element for conditioning air (e.g., a cooling element), or may have no conditioning element integrated within the device, instead receiving already conditioned air (e.g., in passage 110).

Air in cavity 120 is periodically expelled from cavity 120 through outlet 125, which is constricted and shaped so as to generate a vortex ring, such as vortex ring 130. In particular embodiments, outlet 125 may be any suitably shaped aperture, and may be actuated so as to prevent backflow into chamber 120, for example, when the actuator draws back toward the rear of the device (e.g., when permanent magnet 140 draws near electromagnet 135, bringing membrane 145 along with it).

Air in cavity 120 is expelled from cavity 120 by a linear actuator. In the example of FIG. 1, the actuator includes an electromagnet 135 and a permanent magnet 140 attached to membrane 145. In general, membrane 145 may be a flexible membrane, a rigid membrane, or a plate. The actuator may use a syringe, hydraulics, and/or pneumatics to actuate the membrane. When electromagnetic 135 is in a first polarity, electromagnetic 135 attracts permanent magnet 140, drawing magnet 140 near or to electromagnet 135. This action draws membrane 145 back to the rear of cavity 120. When electromagnetic 135 suddenly reverses polarity, magnet 140 is suddenly forced away from electromagnet 135, pushing membrane 145 through cavity 120 and expelling air through outlet 125 to form a vortex ring. In general, the vortex ring is generated due to the friction of the packet of air with the edge of outlet 120. The higher velocity air in the center of outlet 120 will roll towards the edge of outlet 120 as the air moves forward, which creates the torus shape of the vortex ring. Outlet 125 may be circular, in particular embodiments. The dimensions of outlet 125 may be sized based on the size of cavity 120 and/or the desired size of the output vortex rings. For example, outlet 125 may have a radius, diameter, or circumference of 25 cm, in particular embodiments.

Heating element 105 may use joule heating, which involves sending electrical current through a resistive material to generate heat. In general, heating element 105 may be replaced by a temperature control element that uses any suitable heating or cooling method to condition the air in passage 110, such as using a heat pump or refrigeration cycle, sending air in through a central air conditioning or heating system, using heat pipes, using a piezo electric heating element, or using a fuel such as gas. While example device 100 includes a conditioning element (i.e., heating element 105) in passage 110, this disclosure contemplates that air in passage 110 could be already heated or cooled, e.g., from outside device 100, and drawn into cavity 120 (e.g., by a pump system).

In a device that generates toroidal vortices, an actuator (such as actuator 402 of the example device 400 of FIG. 4) that expels air from a device cavity may be any suitable electronically controlled and actuated mechanism of action to generate toroidal vortices. Examples include a rack and pinion mechanism 403 of example device 400 of FIG. 4 or a slider-crank mechanism 404 of example device 400 of FIG. 4 to generate vortex rings. For example, particular embodiments may use a crank shaft mechanism with a flexible membrane or a rigid plate to actuate air in the chamber. Other actuation approaches include ball screws, belt drives, cams, voice coils, solenoids, etc.

In particular embodiments, a membrane such as membrane 145 may be made from any suitable material that is relatively impermeable to air, such as silicone, neoprene, rubber, etc. In particular embodiments, a plate used instead of a membrane may be made from materials such as plastic, metal, acrylic, etc.

Portions of a device for generating vortex rings, including the cavity, the actuator, and the outlet, can be automatically or manually moved, for example in order to adjust the direction of vortex rings created by the system. For example, the cavity can be actuated on a pan and tilt mechanism to orient the outlet to any direction. Automatic movement of the device can be achieved with any actuator such as brushless DC motor (BLD), brushed motor, or other actuator with any kind of transmission with belt drive or gear transmission or cable transmission. As explained below, in particular embodiments a device may reorient its direction in response to the sensed presence and/or location of persons in the environment.

A device for creating vortex rings as described herein may take any suitable form. For example, the device may be a free-standing device, similar to a personal heater. A free-standing device may be used for providing heated air, and/or may be used to provide cooled air by having a passage such as a hose that attaches from the device to an exterior opening, such as a window or door, to expel hot air to the exterior.

As another example, a device described herein for generating vortex rings may take the form of a wall mounted device, for example similar to a mini-split system. As another example, a device described herein for generating vortex rings may take the form of a window-mounted device. As another example, a device described herein for generating vortex rings may take the form of a ceiling-mounted or floor-mounted device, for example similar to a central HVAC system with ceiling or floor vents. In particular embodiments, a device for generating vortex rings may contain one or more filters for filtering or purifying air brought into the device.

Toroidal vortices can travel over, e.g., 60 feet without dissipating, e.g., via turbulence. Conventional fans or laminar flow will become turbulent and dissipate in typically less than 6 feet. Therefore, a device that generates vortex rings as described herein is able to send packets of air much further than conventional fans, and in addition, such devices can efficiently transfer conditioned air, as the same air particles will travel within the vortex ring from the source to the destination. In particular embodiments, a vortex ring transmitted by the devices described herein may be relatively slow moving, and as described more fully below, may be directed to specific locations where people occupy, for example at a desk, in the kitchen, etc. For example, a device that transmits vortex rings may also utilize predictive and tracking technologies to identify, direct, and effectively envelop a person with a personal blanket of air at their preferred temperature, and may predict where a person is likely to go to pre-heat or pre-cool a location or object (e.g., a chair, a blanket, etc.). As a result, the device described herein can provide temperature control by conditioning a much smaller volume of air than typical systems, saving energy and associated resources.

In particular embodiments, a device that generates vortex rings may use those rings for non-temperature-related functionality, such as for dusting, sending reminders, providing aromas, and efficiently circulating air and/or efficiently providing filtered air. In particular embodiments, a device that generates vortex rings may provide both temperature-related and non-temperature-related functionality using vortex rings. For example, dusting is typically a very manual process that requires time and work. However, embodiments of this disclosure use targeted vortex rings to dust surfaces. For example, a device may move in a predetermined pattern and transmit vortex rings while moving in the pattern, so as to dust an area in the environment of the device. As another example, a device may identify objects in its environment (e.g., using sensors such as cameras, along with object-detection methods) and periodically and/or on demand target certain objects with vortex rings in order to dust the object. For example, an object identified as a particular kind of object (e.g., a desk) or as having a suitably large surface area may be automatically dusted by a device using vortex rings. In particular embodiments, a device may use relatively higher-velocity vortex rings for dusting than for other applications (e.g., than for transmitting reminders or for providing conditioned air).

As another example of non-temperature-related functionality, aromas can have an impact on a person's enjoyment of their environment, and can improve a person's mood and reduce stress. Thus, embodiments of this disclosure may use scented vortex rings to deliver aromas to a particular area. For example, a user may be detected in the environment of the device, and the user may be identified as a user who has requested aroma delivery via a vortex ring. The device may then deliver aroma-infused air, traveling as a vortex ring, to the identified user, for example on demand or on a predetermined schedule. In particular embodiments, a vortex ring may be imbued with an aroma through aerosolized mist (e.g., aerosolized mist 405 of example device 400 of FIG. 4) or evaporation or ultrasonic vaporization or other aromatization method. In particular embodiments, air is imbued with aroma within the device for transmitting vortex rings. In particular embodiments, air is imbued with aroma outside of that device and sent to the device (e.g., via a pump and connected tubing, as illustrated by example pump and connected tubing 406 connected to example device 400 of FIG. 4) for transmission via vortex ring.

In particular embodiments, a container (e.g., an air-tight container) can contain a liquid or gel substance that has fragrance such as a perfume or oil. This container may be connected to the vortex ring generating cavity, or may be inside it. In particular embodiments, a heating element may evaporate or vaporize the fragrance to disperse the fragrance inside the vortex ring generating cavity, and the fragrance can then be expelled through the outlet. In particular embodiments, multiple containers, each containing different fragrances, may be contained in and/or connected to a device for generating vortex rings, in order to transmit different fragrances. For example, different fragrances may be associated with different users, e.g., based on user preferences, or may be associated with different reminders, e.g., based on user preferences.

As another example of non-temperature-related functionality, vortex rings may be used to transmit reminders. For example, a device may periodically direct a vortex ring in the direction of a person to remind the person to walk around (e.g., if sitting) or to engage in another activity, such as stretching. As another example, a user can set the device to provide a custom reminder based on timing (e.g., send a puff of air via a vortex ring in 20 minutes) or based on the state of one or more other devices (e.g., send a puff of air via a vortex ring when a smart oven ends a baking cycle). In particular embodiments, such reminders do not emit loud sounds, which can be preferable in many situations to audio-based alarms that can be heard by people whom the alarm is not intended for. In addition, reminders sent by vortex ring do not require the user's active focus on, or engagement with, the reminder system, for example as visual reminders require. Other examples of reminders include reminders to look away from a screen periodically (e.g., every 20 minutes) or a reminder to blink (e.g., when looking at a screen, which can cause dry eyes). In particular embodiments, one or more particular parameters of a vortex ring (e.g., an aroma, a velocity, and/or a number of rings) may be customizable by the user in association with a particular reminder or with particular kinds of reminders. In particular embodiments, one or more parameters of a vortex ring (e.g., an aroma, a velocity, and/or a number of rings) may increase when a system (e.g., an identification system associated with the device or in communication with the device) determines that a user has not responded to a reminder (e.g., vortex rings may be sent with increasing velocity when a user has not gotten up from their desk after being sent a reminder to get up).

Figure 4:
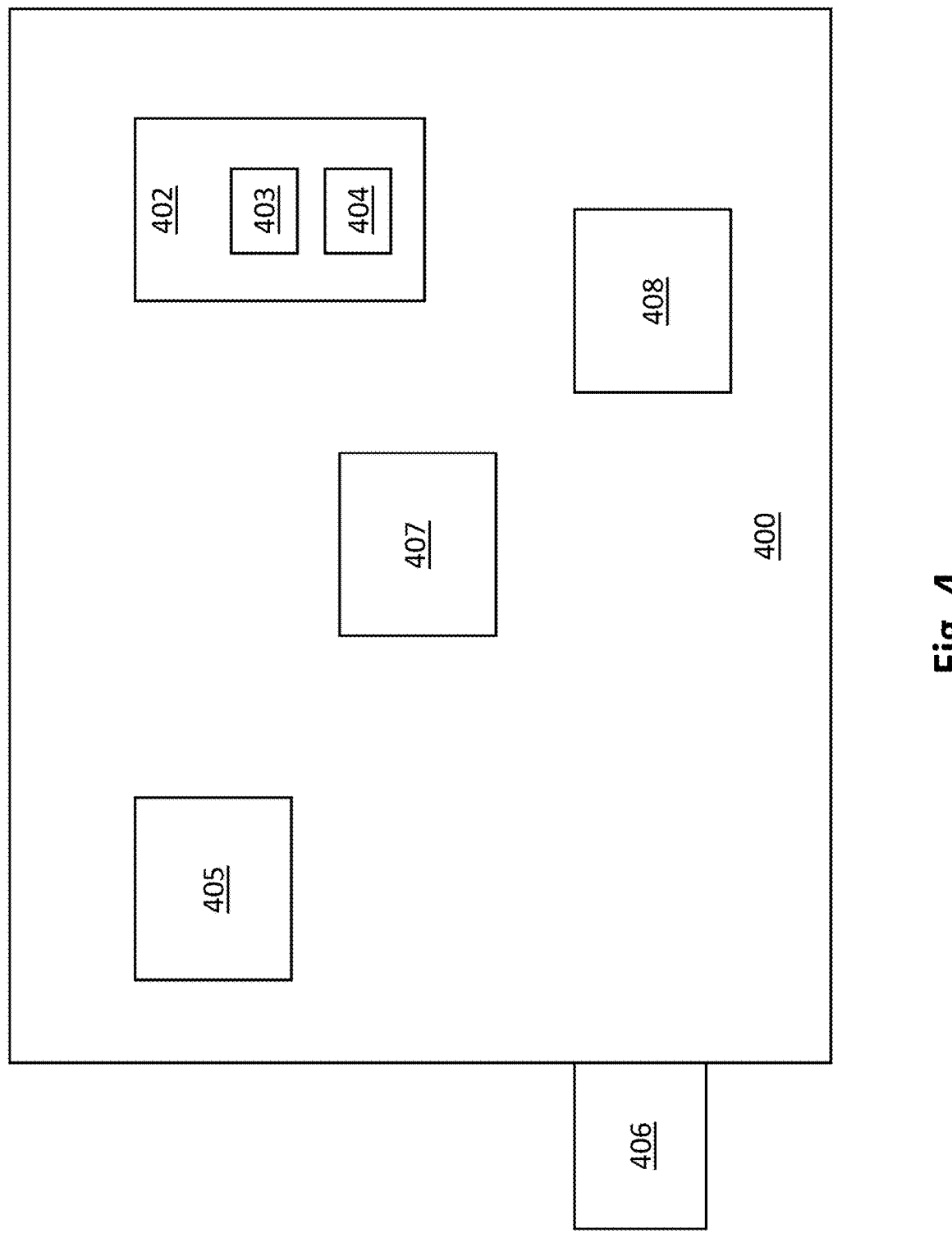
FIG. 4 illustrates another example device for generating toroidal vortices.

In particular embodiments, a device for transmitting vortex rings may use one or more of software, sensors, and actuators, to target and predict the people and locations to which to deliver a vortex ring (e.g., where to delivery conditioned air, where to deliver a reminder, etc.), For example, a device may identify people using sensors (e.g., one or more RGB cameras, one or more IR cameras, etc.) and use movement actuators (e.g., pan and tilt mechanism actuators), such as movement actuator 408 of example device 400 of FIG. 4), to direct vortex rings to those people, as appropriate. In particular embodiments, sensors and software (e.g., face-recognition algorithms) may be used to identify and predict locations that people are moving to, for example in order to follow where people go, as well as to preheat and cool the locations that the people will most likely go to throughout the day, such as beds, desks, and couches. In particular embodiments, an IR sensor or camera can detect the current temperature of people and objects, thereby determining the impact of transmitted vortex rings on the temperature of each person or object, for example in order to determine whether more conditioning or more vortex rings are required to meet a target temperature for a user or region (which target temperature may be set manually or automatically, for example based on previous user settings or historical data for a particular user and/or for particular objects, along with, in particular embodiments, other contextual information such as time of day, etc.).

In particular embodiments, sensors associated with a device may include one or more RGB cameras, one or more DVS cameras, one or more IR sensors, one or more depth sensors, etc. This disclosure contemplates that one or more such sensors may be integrated with a device used to generate vortex rings, or may be integrated in another device that is connected to (e.g., via a wired or wireless connection) to the device generating vortex rings or to an intermediary device (e.g., a computer device, such as a smartphone or other computing device, that coordinates communications and instructions between the sensors and the device that generates vortex rings). Moreover, the processes for detecting and identifying people or objects in an environment may be executed by hardware on the device that generates vortex rings, or may be executed by a connected device.

In particular embodiments, a device may adjust the velocity of a vortex ring in order to have the vortex ring meet a predicted location of an object or a person. For example, if a person is detected as walking, then the device (or a connected computing device) may determine the direction in which to send a vortex ring or series of vortex rings and a velocity at which to transmit the vortex ring so that the ring arrives at the user's future, predicted location (e.g., rather than being directed at the user's current location, which the user will move away from).

In particular embodiments, one or more sensors (such as camera sensor 407 of example device 400 of FIG. 4) may be used to determine whether a surface is dusty, for example based on an image of the surface, and this information may be used to trigger delivery of vortex rings to the surface for dusting or to schedule a time at which to perform dusting (e.g., a time when, for example based on historical user data, a user will not be in the vicinity of the surface to be dusted).

FIG. 2 illustrates an example method for generating toroidal vortices. Step 205 of the example method of FIG. 2 includes receiving air into a device that includes an actuator for generating one or more toroidal vortices. As described above, receiving air may include actively or passively intaking air into the device, e.g., through passage 110 of the example device 100. Step 210 of the example method of FIG. 2 includes determining whether to generate a toroidal vortex for conditioning air in an environment of the device or whether to generate a toroidal vortex for a non-temperature-related functionality. As discussed above, this determination may be made by the device that generates the toroidal vortices, or by a connected device.

Step 215 of the example method of FIG. 2 includes generating, based on the determination and by the actuator, one or more toroidal vortices. As explained above, one or more parameters of one or more toroidal vortices (e.g., temperature, velocity, aroma, location directed to, and/or number) may be adjusted based on the determination made in step 210. As described above, in particular embodiments, these parameters may be based on user preferences, which may be determined in any particular instances based on identification of a particular user. After the one or more toroidal vortices are generated, step 220 of the example method of FIG. 2 includes transmitting, by the device, the one or more toroidal vortices into the environment.

Particular embodiments may repeat one or more steps of the method of FIG. 2 as appropriate. Although this disclosure describes and illustrates particular steps of the method of FIG. 2 as occurring in a particular order, this disclosure contemplates any suitable steps of the method of FIG. 2 occurring in any suitable order. Moreover, although this disclosure describes and illustrates particular components, devices, or systems carrying out particular steps of the method of FIG. 2, this disclosure contemplates any suitable combination of any suitable components, devices, or systems carrying out any suitable steps of the method of FIG. 2. Moreover, this disclosure contemplates that certain steps of the example method illustrated in FIG. 2, may be performed by circuitry of a computing device described herein, by a processor coupled to non-transitory computer readable storage media, or any suitable combination thereof.

Figure 3:
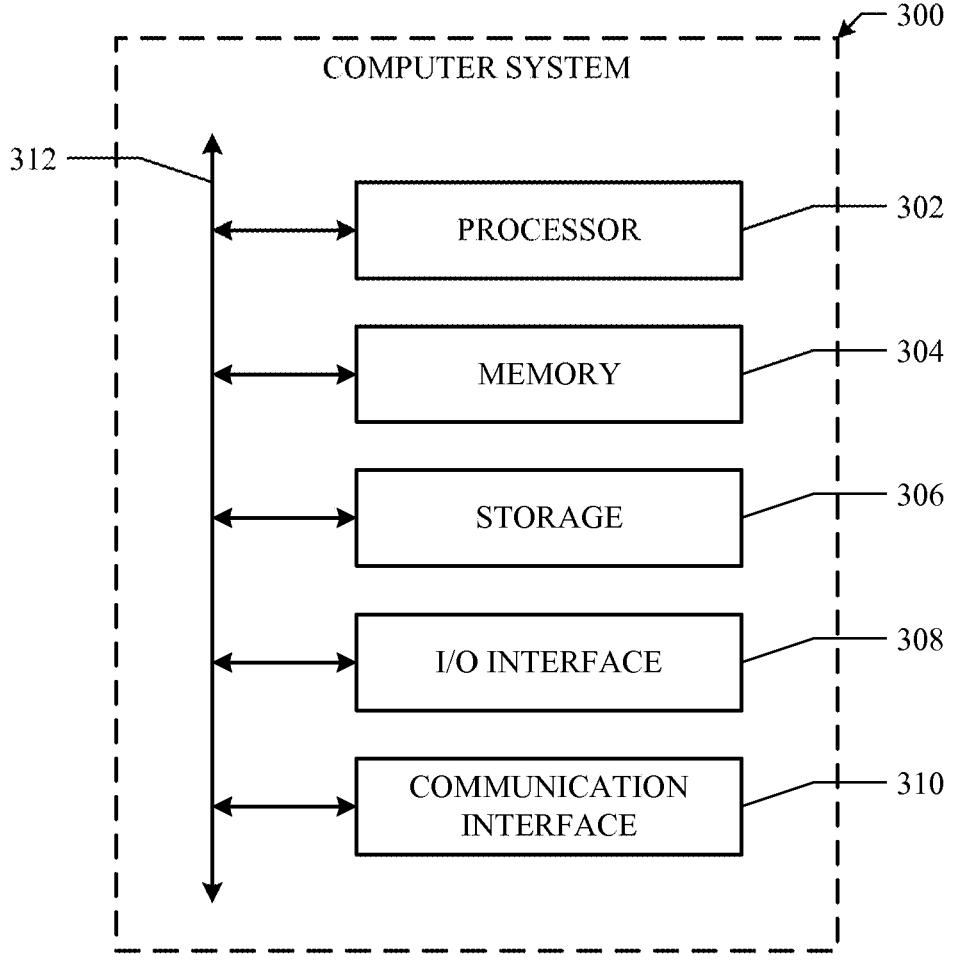
FIG. 3 illustrates an example computing system.

FIG. 3 illustrates an example computer system 300. In particular embodiments, one or more computer systems 300 perform one or more steps of one or more methods described or illustrated herein. In particular embodiments, one or more computer systems 300 provide functionality described or illustrated herein. In particular embodiments, software running on one or more computer systems 300 performs one or more steps of one or more methods described or illustrated herein or provides functionality described or illustrated herein. Particular embodiments include one or more portions of one or more computer systems 300. Herein, reference to a computer system may encompass a computing device, and vice versa, where appropriate. Moreover, reference to a computer system may encompass one or more computer systems, where appropriate.

This disclosure contemplates any suitable number of computer systems 300. This disclosure contemplates computer system 300 taking any suitable physical form. As example and not by way of limitation, computer system 300 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 300 may include one or more computer systems 300; be unitary or distributed; span multiple locations; span multiple machines; span multiple data centers; or reside in a cloud, which may include one or more cloud components in one or more networks. Where appropriate, one or more computer systems 300 may perform without substantial spatial or temporal limitation one or more steps of one or more methods described or illustrated herein. As an example and not by way of limitation, one or more computer systems 300 may perform in real time or in batch mode one or more steps of one or more methods described or illustrated herein. One or more computer systems 300 may perform at different times or at different locations one or more steps of one or more methods described or illustrated herein, where appropriate.

In particular embodiments, computer system 300 includes a processor 302, memory 304, storage 306, an input/output (I/O) interface 308, a communication interface 310, and a bus 312. Although this disclosure describes and illustrates a particular computer system having a particular number of particular components in a particular arrangement, this disclosure contemplates any suitable computer system having any suitable number of any suitable components in any suitable arrangement.

In particular embodiments, processor 302 includes hardware for executing instructions, such as those making up a computer program. As an example and not by way of limitation, to execute instructions, processor 302 may retrieve (or fetch) the instructions from an internal register, an internal cache, memory 304, or storage 306; decode and execute them; and then write one or more results to an internal register, an internal cache, memory 304, or storage 306. In particular embodiments, processor 302 may include one or more internal caches for data, instructions, or addresses. This disclosure contemplates processor 302 including any suitable number of any suitable internal caches, where appropriate. As an example and not by way of limitation, processor 302 may include one or more instruction caches, one or more data caches, and one or more translation lookaside buffers (TLBs). Instructions in the instruction caches may be copies of instructions in memory 304 or storage 306, and the instruction caches may speed up retrieval of those instructions by processor 302. Data in the data caches may be copies of data in memory 304 or storage 306 for instructions executing at processor 302 to operate on; the results of previous instructions executed at processor 302 for access by subsequent instructions executing at processor 302 or for writing to memory 304 or storage 306; or other suitable data. The data caches may speed up read or write operations by processor 302. The TLBs may speed up virtual-address translation for processor 302. In particular embodiments, processor 302 may include one or more internal registers for data, instructions, or addresses. This disclosure contemplates processor 302 including any suitable number of any suitable internal registers, where appropriate. Where appropriate, processor 302 may include one or more arithmetic logic units (ALUs); be a multi-core processor; or include one or more processors 302. Although this disclosure describes and illustrates a particular processor, this disclosure contemplates any suitable processor.

In particular embodiments, memory 304 includes main memory for storing instructions for processor 302 to execute or data for processor 302 to operate on. As an example and not by way of limitation, computer system 300 may load instructions from storage 306 or another source (such as, for example, another computer system 300) to memory 304. Processor 302 may then load the instructions from memory 304 to an internal register or internal cache. To execute the instructions, processor 302 may retrieve the instructions from the internal register or internal cache and decode them. During or after execution of the instructions, processor 302 may write one or more results (which may be intermediate or final results) to the internal register or internal cache. Processor 302 may then write one or more of those results to memory 304. In particular embodiments, processor 302 executes only instructions in one or more internal registers or internal caches or in memory 304 (as opposed to storage 306 or elsewhere) and operates only on data in one or more internal registers or internal caches or in memory 304 (as opposed to storage 306 or elsewhere). One or more memory buses (which may each include an address bus and a data bus) may couple processor 302 to memory 304. Bus 312 may include one or more memory buses, as described below. In particular embodiments, one or more memory management units (MMUs) reside between processor 302 and memory 304 and facilitate accesses to memory 304 requested by processor 302. In particular embodiments, memory 304 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 304 may include one or more memories 304, where appropriate. Although this disclosure describes and illustrates particular memory, this disclosure contemplates any suitable memory.

In particular embodiments, storage 306 includes mass storage for data or instructions. As an example and not by way of limitation, storage 306 may include a hard disk drive (HDD), a floppy disk drive, flash memory, an optical disc, a magneto-optical disc, magnetic tape, or a Universal Serial Bus (USB) drive or a combination of two or more of these. Storage 306 may include removable or non-removable (or fixed) media, where appropriate. Storage 306 may be internal or external to computer system 300, where appropriate. In particular embodiments, storage 306 is non-volatile, solid-state memory. In particular embodiments, storage 306 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 306 taking any suitable physical form. Storage 306 may include one or more storage control units facilitating communication between processor 302 and storage 306, where appropriate. Where appropriate, storage 306 may include one or more storages 306. Although this disclosure describes and illustrates particular storage, this disclosure contemplates any suitable storage.

In particular embodiments, I/O interface 308 includes hardware, software, or both, providing one or more interfaces for communication between computer system 300 and one or more I/O devices. Computer system 300 may include one or more of these I/O devices, where appropriate. One or more of these I/O devices may enable communication between a person and computer system 300. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 308 for them. Where appropriate, I/O interface 308 may include one or more device or software drivers enabling processor 302 to drive one or more of these I/O devices. I/O interface 308 may include one or more I/O interfaces 308, where appropriate. Although this disclosure describes and illustrates a particular I/O interface, this disclosure contemplates any suitable I/O interface.

In particular embodiments, communication interface 310 includes hardware, software, or both providing one or more interfaces for communication (such as, for example, packet-based communication) between computer system 300 and one or more other computer systems 300 or one or more networks. As an example and not by way of limitation, communication interface 310 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 310 for it. As an example and not by way of limitation, computer system 300 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 300 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 300 may include any suitable communication interface 310 for any of these networks, where appropriate. Communication interface 310 may include one or more communication interfaces 310, where appropriate. Although this disclosure describes and illustrates a particular communication interface, this disclosure contemplates any suitable communication interface.

In particular embodiments, bus 312 includes hardware, software, or both coupling components of computer system 300 to each other. As an example and not by way of limitation, bus 312 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 312 may include one or more buses 312, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend.

What is claimed is:

1. A method comprising:
   receiving air into a device comprising an actuator for generating one or more toroidal vortices;
   sensing, by a sensor associated with the device, one or more objects in the environment of the device;
   determining whether to generate a toroidal vortex for dusting at least one of the objects in the environment of the device;
   generating, based on the determination and by the actuator, one or more toroidal vortices; and
   transmitting, by the device, the one or more toroidal vortices to the at least one of the objects in the environment of the device.

2. The method of claim 1, wherein the actuator comprises one or more of a rack-and-pinion mechanism or a slider-crank mechanism.

3. The method of claim 1, further comprising conditioning the received air by at least one of (1) heating the received air or (2) cooling the received air.

4. The method of claim 1, further comprising transmitting a reminder by generating one or more second toroidal vortices and transmitting, by the device, the one or more second toroidal vortices towards a person.

5. The method of claim 1, further comprising transmitting an aroma by scenting the received air according to the aroma, generating one or more second toroidal vortices using the scented received air, and transmitting the one or more toroidal vortices into the environment.

6. The method of claim 3, further comprising determining, based on one or more preferences associated with a person, one or more parameters for heating or cooling the received air.

7. The method of claim 1, wherein:
the at least one of the one or more objects comprises a surface; and
the method further comprises determining, based on a detected dust on the surface, to dust the surface using the one or more toroidal vortices.

8. The method of claim 1, further comprising determining, based on the at least one of the one or more objects, a transmission direction for the one or more toroidal vortices.

9. The method of claim 1, further comprising:
predicting a future location of a person in the environment the device; and
determining, based on the predicted future location, a particular location in the environment to direct one or more second toroidal vortices to.

10. An apparatus comprising:
an intake for receiving air into the apparatus;
an outlet for transmitting one or more toroidal vortices from the apparatus;
a sensor configured to detect one or more objects in the environment of the apparatus;
one or more non-transitory computer readable storage media storing instructions; and one or more processors coupled to the non-transitory computer readable storage media, the one or more processors operable to execute the instructions to determine whether to generate a toroidal vortex for dusting at least one of the objects in the environment of the device; and
an actuator configured to generate the or more toroidal vortices through the outlet of the apparatus to the at least one of the objects in the environment of the device.

11. The apparatus of claim 10, wherein the actuator comprises one or more of a rack-and-pinion mechanism or a slider-crank mechanism.

12. One or more non-transitory computer readable storage media storing instructions and coupled to one or more processors that are operable to execute the instructions to:
sense, by a sensor associated with the device, one or more objects in the environment of a device for generating toroidal vortices;
determine whether to generate a toroidal vortex for dusting at least one of the objects in the environment of the device;
transmitting, based on the determination, an instruction to an actuator of the device to generate one or more toroidal vortices and transmit the one or more toroidal vortices to the at least one of the objects in the environment of the device.

13. The media of claim 12, wherein the actuator comprises one or more of a rack-and-pinion mechanism or a slider-crank mechanism.

14. The apparatus of claim 10, wherein the one or more processors are further operable to execute the instructions to determine whether to condition the received air by at least one of (1) heating the received air or (2) cooling the received air.

15. The apparatus of claim 14, wherein the one or more processors are further operable to execute the instructions to determine, based on one or more preferences associated with a person, one or more parameters for heating or cooling the received air.

16. The apparatus of claim 10, wherein the one or more processors are further operable to execute the instructions to transmit a reminder by instructing the actuator to generate one or more second toroidal vortices and transmit the one or more second toroidal vortices towards a person.

17. The apparatus of claim 10, wherein:
the at least one of the one or more objects comprises a surface; and
the one or more processors are further operable to execute the instructions to determine, based on a detected dust on the surface, to dust the surface using the one or more toroidal vortices.

18. The apparatus of claim 10, wherein the one or more processors are further operable to execute the instructions to determine, based on the at least one of the one or more objects, a transmission direction for the one or more toroidal vortices.

19. The apparatus of claim 10, wherein the one or more processors are further operable to execute the instructions to:
predict a future location a person in the environment the device; and
determine, based on the predicted future location, a particular location in the environment to direct one or more second toroidal vortices to.

* * * * *